United States Patent [19]

Spenleuhauer et al.

[11] Patent Number: 5,766,635
[45] Date of Patent: Jun. 16, 1998

[54] PROCESS FOR PREPARING NANOPARTICLES

[75] Inventors: Gilles Spenleuhauer, Cachan; Didier Bazile, La Varenne-S.-Hilaire; Michel Veillard, Sceaux; Christian Prud'Homme; Jean-Paul Michalon, both of Lyons, all of France

[73] Assignee: Rhone-Poulenc Rorer S.A., Antony Cedex, France

[21] Appl. No.: 462,946

[22] Filed: Jun. 5, 1995

Related U.S. Application Data

[63] Continuation of Ser. No. 110,043, filed as PCT/FR92/00582, Jun. 25, 1992, abandoned.

[51] Int. Cl.$^6$ .................................. A61K 9/14; A61K 9/51
[52] U.S. Cl. ........................... 424/489; 528/491; 528/493
[58] Field of Search ......................... 424/489; 528/423, 528/489

[56] References Cited

U.S. PATENT DOCUMENTS

| | | | |
|---|---|---|---|
| 4,542,025 | 9/1985 | Tire et al. | 424/497 |
| 4,897,267 | 1/1990 | Bontemps et al. | 424/422 |
| 4,981,696 | 1/1991 | Foomis et al. | 424/496 |
| 5,019,400 | 5/1991 | Gombotz et al. | 424/489 |
| 5,145,684 | 9/1992 | Liversidge et al. | 424/489 |
| 5,417,982 | 5/1995 | Modi | 424/488 |

FOREIGN PATENT DOCUMENTS

| | | |
|---|---|---|
| 0 166 596 | 6/1985 | European Pat. Off. |
| 0 275 796 | 12/1987 | European Pat. Off. |

*Primary Examiner*—Peter F. Kulkosky
*Attorney, Agent, or Firm*—Ross J. Oehler

[57] ABSTRACT

Nanoparticles are prepared by dissolving a poly(ethylene oxide) and/or poly(propylene oxide) polylactic copolymer in an organic solvent followed by formation of nanoparticles by mixing the solution containing the polymer with an aqueous solution and by precipitation, without using an additional colloidal protective agent or by microfluidization and solvent evaporation. Nanoparticles prepared by this method are disclosed.

25 Claims, No Drawings

PROCESS FOR PREPARING NANOPARTICLES

CROSS-REFERENCE TO RELATED APPLICATION

This is a continuation of application Ser. No. 08/110,043 filed on Aug. 20, 1993 now abandoned, which is a continuation-in-part application of our co-pending Patent Cooperation Treaty Application Serial No. PCT/FR92/00582, filed Jun. 25, 1992.

FIELD OF THE INVENTION

The present invention relates to processes for preparing small spherical particles, often smaller than 500 nm, capable of transporting or targeting an active principle in a pharmaceutical composition. These particles, referred to herein as "nanoparticles," have the advantage of being able to circulate in the bloodstream without there being a problem of size in the capillaries. The invention also relates to new nanoparticles obtained by the process of the invention and to their use in human or animal pharmacy.

BACKGROUND OF THE INVENTION

It is known from the prior art, described in Patent FR 2,608,988, to prepare particles smaller than 500 nm in size by at least three types of process. The first process type consists of polymerization of a monomer in a solution so as to obtain a micellar dispersion of the polymer in the solution. This first process type is limited to monomers which can be polymerized in solution. Moreover, it necessitates removal, after the polymerization step, of the polymerization catalyst, the low molecular weight oligomers, the monomers and the surfactants needed for the polymerization. The polymer obtained in this first process type has a random molecular weight distribution.

The second and third process types use preformed polymers, dissolving them in a solvent, forming a precipitate or a dispersion from a solution of these polymers and a non-solvent, and then evaporating off the solvent to recover the nanoparticles in the form of a colloidal suspension. The solvent solution is generally an organic solution of the polymer, and the nonsolvent solution is often an aqueous solution.

According to the second type of process, the polymer is dissolved in a water-miscible organic solvent. When the resulting solution is mixed with the aqueous phase, the polymer insoluble in the aqueous phase/organic solvent mixture precipitates in the form of nanoparticles.

According to the third type of process, a water immiscible organic solvent containing the polymer is emulsified in an aqueous phase, and the organic solvent is then evaporated off.

Formation of the precipitate or the emulsion requires the presence of a considerable amount of surfactant. It is very difficult to remove the surfactant remaining in the colloidal suspension during the subsequent evaporation to obtain the nanoparticles. Furthermore, the presence of a surfactant is often undesirable in the interest of good biocompatibility. Hence the latter two techniques cannot be used for the preparation of biocompatible nanoparticles because a colloidal protective agent is present.

FR 2,608,988 relates to a process for preparing dispersible colloidal systems in the form of nanoparticles smaller than 500 nm. These nanoparticles, based on a substance which can be a polymer and/or an active principle, are obtained by the second method mentioned above. The nanoparticles which are obtained, based on a polylactic polymer, contain an amount of surfactant equal to the amount of polymer in the majority of the examples. In only one example (Example 4) does the inventor claim to obtain nanoparticles of polylactic polymer without a surfactant. The Applicants reproduced this experiment and obtained nanoparticles of polylactic polymer from an acetone solution of polylactic acid and water with extremely low yields, always less than 10%. Hence this technique cannot practicably be used for the preparation of nanoparticles of polylactic acid in the absence of a surfactant.

BRIEF SUMMARY OF THE INVENTION

The present invention is directed to preparing nanoparticles from polymers containing a majority of degradable units in the absence of a surfactant. In particular, the invention comprises preparing nanoparticles from poly (ethylene oxide) and/or poly(propylene oxide) polylactic copolymer in the absence of a surfactant or of an additional colloidal protective agent, using a copolymer containing a majority of polylactic units modified by incorporation of poly(ethylene oxide) and/or poly(propylene oxide) units.

DETAILED DESCRIPTION OF PREFERRED EMBODIMENTS

According to the present invention there is provided a process for preparing nanoparticles which comprises dissolving poly(ethylene oxide) and/or poly(propylene oxide) polylactic (PLA) copolymer containing a majority of units of formula:

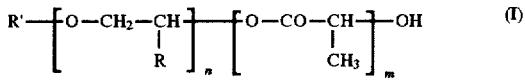

in which R, independently in each of the alkylene oxide units, represents hydrogen or a methyl group;

R' represents hydrogen or an alkyl unit containing 1 to 4 carbon atoms, preferably a methyl group;

n is an integer between 20 and 1000; and m is an integer between 10 and 1500, in an organic solvent, and mixing the organic solution containing the polymer thus obtained with an aqueous solution, without using an additional colloidal protective agent.

The polylactic unit of this copolymer preferably has a molecular weight of between 700 and 100,000; the poly (ethylene oxide) and/or poly(propylene oxide) unit preferably has a molecular weight of between 1,000 and 40,000. Still more preferably, the polylactic polymeric unit has a molecular weight of between 1,000 and 60,000, and the poly(ethylene oxide) and/or poly(propylene oxide) unit has a molecular weight of between 1,000 and 6,000.

Preferably, the polylactic polymer is a polymer containing 50% of lactic units of D configuration (PLA$_{50}$) and the poly(oxide) is a poly(ethylene oxide).

These polymers preferably take the form of a diblock, i.e., according to a practical manner of implementation, the starting material is a monofunctional commercial polyethylene and/or polypropylene glycol in which R' preferably represents a methyl group, of desired molecular weight, i.e. of molecular weight between 1,000 and 40,000, or alternatively containing approximately 20 to 1,000 ethylene oxide or propylene oxide units, and preferably containing 20 to 150 ethylene oxide units or 20 to 100 propylene oxide units (i.e. R=Me), onto which starting material lactide units are grafted until the desired molecular weight is obtained on the polylactic chain, in the presence of a catalyst, such as tin octoate.

To obtain polylactic blocks of molecular weight between 1,000 and 60,000, it is desirable to introduce between approximately 10 and 1,000 lactide units. It is presently most especially preferable to use polylactic poly(ethylene oxide) and/or poly(propylene oxide) copolymers in which the chain contains between 10 and 150 lactic units.

It is still more especially preferable to start with a commercial polyethylene glycol of molecular weight 2,100 containing 48 ethylene oxide units, which is reacted with 40 to 150 lactide units, i.e. to use a compound of formula (I) in which R is hydrogen, R' is methyl, n is 48 and m is between 40 and 150.

After polymerization in solution, the polymers obtained are purified so as to remove the catalyst and the remaining lactide completely. This purification is performed by precipitation of the polymer using a non-solvent or by gel exclusion chromatography. The copolymer is then dried and stored in pulverulent form.

According to a first process for preparing the nanoparticles according to the invention, the desired poly(ethylene oxide) and/or poly(propylene oxide) polylactic polymer is dissolved in a solvent or in a mixture of solvents, and the organic solution is then poured into an aqueous solution so as to cause precipitation of the nanoparticles. No additional colloidal protective agent is used in this process. The term "colloidal agent", which include surfactants, will be understood to mean an agent which promotes colloid formation.

The solvent or mixture of solvents in which the copolymer is soluble is typically a ketone, such as acetone, a cyclic ether, such as tetrahydrofuran, a dioxane, or a nitrile, such as acetonitrile. Acetone is presently preferred. The solubility of the copolymer in these solvents should be at least 10 g/l.

The volume ratio between the aqueous solution and the solution of the copolymer is preferably between 0.5 and 10, and most especially between 1 and 10. The amount of copolymer introduced into the solvent naturally depends on its solubility but to obtain an optimum yield of nanoparticles, an amount of between 10 and 50 mg/ml is preferable.

According to a second process for preparing the nanoparticles, the poly(ethylene oxide) and/or poly (propylene oxide) polylactic polymer is dissolved in an ester, preferably ethyl acetate, and the organic solution is then poured into the aqueous solution. The nanoparticles are formed by using a microfluidizer.

The solvent of the copolymer is then evaporated off by heating the colloidal solution of nanoparticles above the boiling point of the solvent in the case where the removal is performed at atmospheric pressure, or at a temperature below the boiling point of the solvent if the evaporation is performed under reduced pressure. After the solvent has been removed, the suspension of nanoparticles in water is filtered through a filter of pore diameter approximately 1 µm so as to remove aggregates and large particles. The yield of nanoparticles obtained generally exceeds 50%.

The formation of nanoparticles may be performed in the presence of a pharmaceutical active principle, which may be introduced either in the solvent of the copolymer or in the precipitation solvent. Suitable pharmaceutical active principles include spiramycin, taxanes, such as Taxotere® (docetaxel) and taxol. It will be appreciated by one skilled in the pharmaceutical arts that other active principles may be used in accordance with the present invention. The active principle should preferably be soluble in the solvent of the polymer and insoluble in water. Although it is still possible to form nanoparticles if the active principle is soluble in water, the yield thereof may be reduced.

The nanoparticles obtained, which also form part of the present invention, contain only the polymer of formula (I), and optionally an active principle if the precipitation is performed in the presence of an active principle. The nanoparticles generally have an average diameter of between 50 and 500 nm, and preferably an average diameter of between 50 and 250 nm.

The nanoparticles obtained may be used in many fields, such as agrochemistry, reprography paper and photographic paper but, as a result of their fully biocompatible nature, are intended more especially for the human or animal pharmaceutical industry. These products may be injected intramuscularly, subcutaneously, intra-arterially, intravenously, into organs or into cavities without risk of an anaphylactic reaction.

The following non-limiting Examples illustrate the invention in further detail.

EXAMPLE 1

Preparation of Polyethylene Glycol (PEG) Polylactic Copolymers 1.1) polymer PLA $_{50}{}^{2900}$-PEG$^{2100}$ The following are introduced into a 250 ml three-necked round-bottomed flask equipped with a paddle stirrer and a reflux condenser and under a stream of dry nitrogen, the flask being heated on a temperature-regulated oil bath:

| | |
|---|---|
| DL-lactide | 144 g |
| polyethylene glycol | 79.3 g |
| stannous octoate | 0.256 g |
| toluene, distilled | 335 g |

The lactide is recrystallized on the previous day in ethyl acetate, and then washed on the day of the preparation with ethyl ether. It is dried under vacuum. All the reactants are charged, and the mixture is then heated under gentle reflux (110°–114° C.) for 5 and a half hours. The solvent is then removed under vacuum using a rotary evaporator (40 mm Hg −100° C. ). A concentrate (226.3 g) is obtained.

Purification of the copolymer is performed in the following manner:

The following are charged:

| | |
|---|---|
| concentrate | 215 g |
| dichloromethane | 280 g |

The mixture is stirred until a homogeneous solution is formed. This solution is poured slowly into hexane (900 ml) in the cold state. The polymer precipitates in the form of a paste, which is separated after settling has taken place. The polymerization catalyst is removed in the hexane phase. After separation of the polymer, it is dried in an oven under vacuum at 40° C. A copolymer (188.4 g) is obtained, the mass of which is analyzed by nuclear magnetic resonance; the mass of polyethylene glycol is 2,100 and that of polylactic 2,900, representing 40 lactic units and 48 ethylene oxide units.

1.2) polymer PLA$_{50}^{9600}$-PEG$^{2100}$

Example 1.1 is repeated, introducing the following compounds:

| | |
|---|---|
| DL-lactide | 48.6 g |
| polyethylene glycol | 10 g |
| stannous octoate | 0.085 g |
| toluene, distilled | 90 g |

After reaction, a concentrate (63.6 g) is obtained, which is purified by the following method: concentrate (40 g) is dissolved in dichloromethane (200 g) until a homogeneous solution is obtained. This solution is poured slowly into water (800 ml) maintained at between 55 and 60° C. The polymer precipitates and the dichloromethane is evaporated off, the unreacted lactide remains in aqueous solution and the polymer is centrifuged and then dried in an oven under vacuum at 40° C.

A polymer (35 g) is obtained, analysis of which by nuclear magnetic resonance enables the molecular weight to be determined. The latter is 9,600 for the lactic chain and 2,100 for the poly(ethylene oxide) chain, representing 133 lactic units and 48 ethylene oxide units.

1.3) polymer PLA$_{50}^{40000}$

Xylene (180 g) distilled before use, and tin octoate (0.180 g) are introduced into a one-liter reactor heated on an oil bath and equipped with an anchor-shaped stirrer and a reflux condenser and maintained under nitrogen. The mixture is heated, and DL-lactide S(120 g) (Boehringer) recrystallized beforehand in ethyl acetate and washed with sulphuric ether, is then introduced.

The mixture is allowed to react for 5 hours at 140° C. and, at the end of the reaction, it is cooled rapidly and a portion of the xylene is then removed under vacuum. The polymer is dissolved in dichloromethane and precipitated with methanol. It is dried in a vacuum oven at 65° C.

EXAMPLE 2

Preparation of Nonoparticles From These Polymers

The copolymer (50 mg) prepared in Example 1.1 above is used, this being dissolved in acetone (0.5, 2.5, 5 and 10 ml). The nanoparticles are prepared by precipitation, pouring this volume slowly into water (5 ml). The colloidal suspension obtained is evaporated for 30 minutes in a rotary evaporator at room temperature and at a pressure of 3 mm Hg. The suspension is then filtered through a 1.2 μm filter in order to remove large particles and aggregates. The particle diameter and also the yield of production of the particles with respect to the polymer introduced are shown in the table below.

| Water:acetone | 10:1 | 2:1 | 1:1 | 0.5:1 |
|---|---|---|---|---|
| Yield | 75% | 76% | 92% | 79% |
| Diameter (nm) | 67 ± 36 | 63 ± 30 | 50 ± 21 | 38 ± 10 |

EXAMPLE 3 (Comparative)

Comparative Example According to Example 4 of FR 2, 608,988

The same protocol is used, but with the lactic polymer of Example 1.3, of molecular weight 40,000. The nanoparticles are prepared by precipitation, pouring the acetone solution into water (5 ml). The acetone is evaporated off in a rotary evaporator for 30 minutes. During this phase, the polymer precipitates and sticks to the walls. The suspension is collected and filtered through a filter 1.2 μm in diameter. The filtrate is completely clear. The polymer concentration is too low to be measurable.

EXAMPLE 4

Preparation of Nanoparticles Containing an Active Principle

Spiramycin (40 mg) and the copolymer (200 mg) prepared according to point 1.2 above are dissolved in acetone (2 ml). The nanoparticles are prepared by precipitation, pouring the acetone solution into 0.1M phosphate buffer, pH 7.4 (20 ml).

The acetone is evaporated off in a rotary evaporator for 30 minutes, and the solution is then filtered through a 1.2 μm filter. Nanoparticles of spiramycin and copolymer 74 nm in diameter are obtained.

EXAMPLE 5

Preparation of Nanoparticles of Polymer PLA$_{50}^{30000}$-PEG$^{2000}$ Containing an Active Principle 24 mg of copolymer PLA$_{50}^{30000}$-PEG$^{2000}$, 67.5 mg of PLA$_{50}$ having a molecular weight of 60,000 and 10 mg Taxotere® (docetaxel) are dissolved in 5 ml of acetone. The nanoparticles are prepared by precipitation, pouring the acetone solution into 10 ml of water. The acetone is evaporated off in a rotary evaporator for 60 minutes. The suspension is then filtered on a filter of 1.2 μm. Nanoparticles of Taxotere® and copolymer 135±44 nm are obtained.

EXAMPLE 6

Preparation and Nanoparticles of PLA$_{50}^{30000}$-PEG$^{5000}$ Containing an Active Principle The same procedures as Example 5 are used with 24 mg of PLA$_{50}^{30000}$-PEG$^{5000}$. Nanoparticles of Taxotere® and copolymer of 152±55 nm are obtained.

EXAMPLE 7

Preparation of Nanoparticles by Microfluidization Without Surfactant

The polymer (100 mg) is solubilized in ethyl acetate (1 ml). This organic solution is poured into water (10 ml) with stirring using an Ultraturrax. After 30 seconds of stirring, the emulsion is homogenized and fined for 2 minutes by recycling using a microfluidizer (MICROFLUIDICS 110 S). The ethyl acetate is removed by evaporation under partial vacuum for 45 minutes, and the nanoparticles are then filtered through a SARTORIUS or MILLIPORE filter of porosity 1.2 μm.

| EXPERIMENT | NATURE OF THE PLA-PEG COPOLYMER | SIZE (nm) | YIELD (%) |
|---|---|---|---|
| 1 | 2900/2100 | 65 | 71 |
| 2 | 9600/2100 | 100 | 85 |
| 3 | 8000/4000 | 60 | 87 |
| 4 | 16000/4000 | 120 | 61.2 |
| 5 | 30000/2000 | 280 | N.D |
| 6 | 30000/5000 | 150 | 65.5 |
| C1 | 52000/0 | IMPRACTICABLE, INSTANTANEOUS PRECIPITATION OF THE POLYMER | |

N.B.: Experiments 1 and 2 refer to the preparations of Examples 1.1 and 1.2, respectively. Experiment C1 refers to a comparative example using procedures similar to those set forth in the Examples above but using 100 g of a polylactic polymer (MW 52000). The copolymers 8000/4000, 16000/4000, 36000/2000 and 30000/5000 (Experiments 3, 4, 5 and 6, respectively) are prepared in the same manner as Example 1 from the following amounts of polyethylene glycol, DL-lactide, toluene and tin octoate:

| EXPER- | PEG | | DL | TOL- | TIN |
|---|---|---|---|---|---|
| IMENT | NATURE | WEIGHT | LACTIDE | UENE | OCTOATE |
| 3 | 4000 | 13 g | 26 g | 40 g | 0.5 |
| 4 | 4000 | 10 g | 40 g | 60 g | 0.08 g |
| 5 | 2000 | 2.5 g | 37.5 g | 60 g | 0.08 g |
| 6 | 5000 (methyl ester) | 5 g | 30 g | 45 g | 0.06 g |

We claim:

1. A process for preparing narloparticles comprising dissolving a poly(ethylene oxide) and/or poly(propylene oxide) polylactic copolymer comprising units of Formula I:

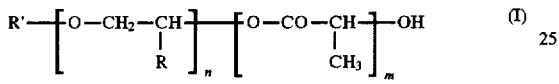

in which R, independently in each of the alkylene oxide units, represents hydrogen or a methyl group;

R' represents hydrogen or an alkyl unit containing 1 to 4 carbon atoms;

n is an integer of about 20 to about 1000; and m is an integer of about 10 to about 1500, in an organic solvent to form an organic solution, and mixing the organic solution with an aqueous solutions in the absence of an additional colloidal protective agent, which includes surfactants.

2. The process according to claim 1, wherein n is about 20 to about 150 and m is about 10 to about 1000.

3. The process according to claim 1, wherein R represents a methyl group, R' represents a methyl group and n is about 20 to about 100.

4. The process according to claim 3, wherein R represents hydrogen, R' represents a methyl group, n is 48, and m is about 40 to about 150.

5. The process according to claim 1, wherein the organic solvent is selected from the group consisting of a ketone, ether, dioxane and nitrile.

6. The process according to claim 5, wherein the solvent is acetone.

7. The process according to claim 1, wherein the volume ratio between the aqueous solution and the organic solution is about 0.5:1 to about 10:1.

8. The process according to claim 1, wherein the concentration of the copolymer in the organic solution is not less than about 10 g/l.

9. The process according claim 1, further comprising introducing a pharmaceutically active principle into the organic solution or the aqueous solution.

10. The process according to claim 9, wherein the pharmaceutically active principle comprises a taxane or spiramycin.

11. A precipitated nanoparticle prepared according to the method of claim 1.

12. The nanoparticle according to claim 11, wherein a plurality of nanoparticles has an average diameter of about 50 to about 500 nm.

13. The nanoparticle according to claim 12, wherein the average diameter is about 50 to about 250 nm.

14. The nanoparticle according to claim 11, further comprising a pharmaceutically active principle.

15. The nanoparticle according to claim 14 wherein the active principle comprises a taxane or spiramycin.

16. The nanoparticle according to claim 15, wherein the taxane comprises docetaxel.

17. A process for preparing nanoparticles comprising the steps of dissolving a poly(ethylene oxide) and/or poly(propylene oxide) polylactic copolymer comprising units of Formula I:

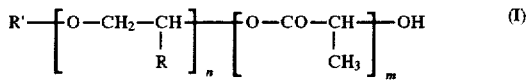

in which R, independently in each of the alkylene oxide units, represents hydrogen or a methyl group;

R' represents hydrogen or an alkyl unit containing 1 to 4 carbon atoms;

n is an integer of about 20 to about 1000; and m is an integer of about 10 to about 1500, in an organic solvent to form an organic solution, and mixing the organic solution with an aqueous solution to cause precipitation of the nanoparticles, wherein the process steps are conducted in the absence of an additional colloidal protective agent, which includes surfactants.

18. A process for preparing nanoparticles comprising the steps of dissolving a poly(ethylene oxide) and/or poly(propylene oxide) potylactic copolymer comprising units of Formula I:

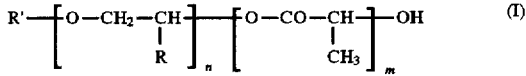

in which R, independently in each of the alkylene oxide units, represents hydrogen or a methyl group;

R' represents hydrogen or an alkyl unit containing 1 to 4 carbon atoms;

n is an integer of about 20 to about 1000; and m is an integer of about 10 to about 1500, in an organic solvent to form an organic solution, mixing the organic solution with an aqueous solution to form a precipitated solution, and microfluidizing the precipitated solution, wherein the process steps are conducted in the absence of an additional colloidal protective agent, which includes surfactants.

19. A nanopartide prepared according to the process of claim 18.

20. The nanoparticle according to claim 19, wherein a plurality of nanoparticles has an average diameter of about 50 to about 500 nm.

21. The nanoparticle according to claim 20, wherein the average diameter is about 50 to about 250 nm.

22. The nanoparticle according to claim 19 in human or animal pharmacy.

23. The nanoparticle according to claim 19, further comprising a pharmaceutically active principle.

24. The nanoparticle according to claim 23, wherein the active principle comprises a taxane or spiramycin.

25. The nanoparticle according to claim 24, wherein the taxane comprises docetaxel.

* * * * *

UNITED STATES PATENT AND TRADEMARK OFFICE
CERTIFICATE OF CORRECTION

PATENT NO.    : 5,766,635
DATED         : June 16, 1998
INVENTOR(S)   : Gilles Spenleuhauer, et. al.

It is certified that error appears in the above-identified patent and that said Letters Patent is hereby corrected as shown below:

On the title page, item:

[30]   Foreign Application Priority Data

June 28, 1991  [FR]       France           9108042

Signed and Sealed this

Sixth Day of October, 1998

Attest:

BRUCE LEHMAN

Attesting Officer            Commissioner of Patents and Trademarks